United States Patent
Ma et al.

(10) Patent No.: US 12,043,830 B2
(45) Date of Patent: Jul. 23, 2024

(54) APPLICATION OF PROKARYOTIC ARGONAUTE PROTEIN WITH ONLY RNA TARGET CLEAVAGE ACTIVITY IN RNA EDITING

(71) Applicant: Hubei University, Wuhan (CN)

(72) Inventors: Lixin Ma, Wuhan (CN); Qi Liu, Wuhan (CN); Yang Liu, Wuhan (CN); Fei Wang, Wuhan (CN); Wanping Chen, Wuhan (CN)

(73) Assignee: HUBEI UNIVERSITY, Wuhan (CN)

( * ) Notice: Subject to any disclaimer, the term of this patent is extended or adjusted under 35 U.S.C. 154(b) by 0 days.

(21) Appl. No.: 18/512,068

(22) Filed: Nov. 17, 2023

(65) Prior Publication Data
US 2024/0110178 A1   Apr. 4, 2024

Related U.S. Application Data

(63) Continuation of application No. PCT/CN2023/095975, filed on May 24, 2023.

(30) Foreign Application Priority Data

Jul. 7, 2022 (CN) .......................... 202210794665.9

(51) Int. Cl.
*C12N 15/11* (2006.01)
*C12N 9/22* (2006.01)

(52) U.S. Cl.
CPC .............. *C12N 15/111* (2013.01); *C12N 9/22* (2013.01)

(58) Field of Classification Search
CPC ................................. C12N 15/111; C12N 9/22
See application file for complete search history.

(56) References Cited

U.S. PATENT DOCUMENTS

2017/0175104 A1* 6/2017 Doudna .................. C12N 15/10
2017/0198306 A1* 7/2017 Valton .................... C12N 15/90

OTHER PUBLICATIONS

Lin, M-W et al. "Enhancing the yield and activity of defucosylated antibody produced by CHO-K1 cells using Cas13d-mediated multiplex gene targeting". Journal of the Taiwan Institute of Chemical Engineers, vol. 121 (2021), pp. 38-47 (Year: 2021).*
Qu, J. et al. "Identification of a Novel cleavage site and confirmation of the effectiveness of NgAgo gene editing on RNA targets". Molecular Biotechnology, vol. 63 (2021), pp. 1183-1191 (Year: 2021).*
MAG: hypothetical protein IPK15_26360 [Verrucomicrobia bacterium], GenBank: MBK8002123.1, pp. 1-2.
CNIPA, Notification of First Office Action for CN202210794665.9, Jul. 19, 2023.
Hubei University (Applicant), Reply to Notification of First Office Action for CN202210794665.9, w/ replacement claims, Aug. 29, 2023.
Hubei University (Applicant), Supplemental Reply to Notification of First Office Action for CN202210794665.9, w/ (allowed) replacement claims, Sep. 1, 2023.
CNIPA, Notification to grant patent right for invention in CN202210794665.9, Sep. 14, 2023.

* cited by examiner

*Primary Examiner* — Neil P Hammell
*Assistant Examiner* — Alexandra Geraldine Dace Denito
(74) *Attorney, Agent, or Firm* — Zhigang Ma

(57) ABSTRACT

An application of a prokaryotic Argonaute protein with only a cleavage activity of a target ribonucleic acid (RNA) in RNA editing is provided. The Argonaute protein is derived from a mesophilic prokaryotes *Verrucomimicrobia bacterium*, and its amino acid sequence is shown in SEQ ID NO: 1 or a protein with high similarity to SEQ ID NO: 1 and the same function. This protein has binding activity to a single-stranded guide DNA and nuclease activity only to the target RNA complementarily paired with the single-stranded guide DNA. Therefore, the protein can be utilized for in vitro and in vivo targeted RNA editing, providing a new powerful tool for RNA editing.

3 Claims, 6 Drawing Sheets

Figure 1:
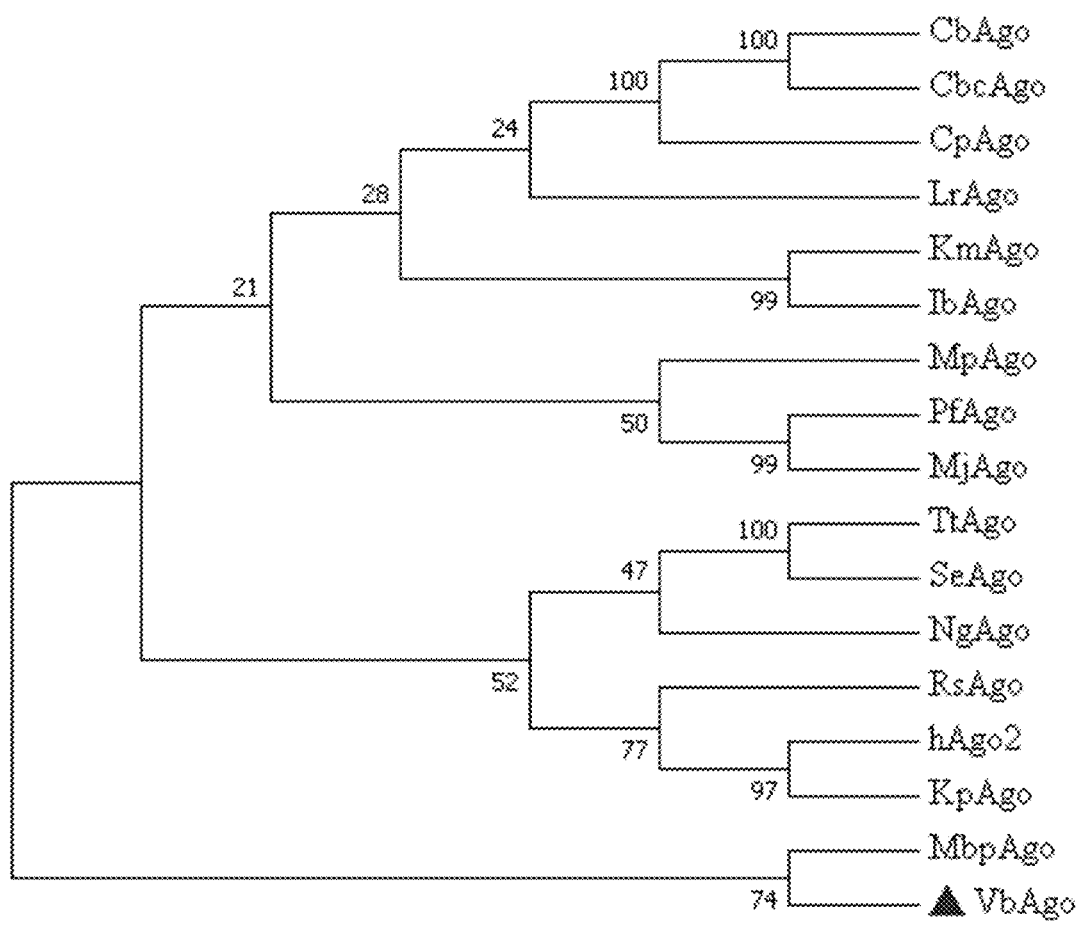

Specification includes a Sequence Listing.

| | Protein | Source | D | E | D | D | Identity (%) |
|---|---|---|---|---|---|---|---|
| SEQ ID NO: 3 | KmAgo | Kurthia massiliensis | FIGIDVSH--- | ILAGEKIDDT | TIHRDGFWR | IHYADLGAT | 15.91 |
| SEQ ID NO: 4 | TtAgo | Thermus thermophilus | AVGFDAGGR-- | AQAGERIPQE | LLLRDGRVP | LHLADRLVK | 14.44 |
| SEQ ID NO: 5 | CbAgo | Clostridium butyricum | FIGLDVGTR-- | PQSGEKIAET | VIHRDGFSR | TGYAD--KI | 15.64 |
| SEQ ID NO: 6 | NgAgo | Natronobacterium gregoryi | FIGIDVSRS-- | PQLGEKLQST | VIHRDGFMN | TAYADQAST | 16.50 |
| SEQ ID NO: 7 | RsAgo | Rhodobacter Sphaeroides | VVGMGLAELS | EYEGYSDAIR | VFHAHRPLK | IFYSERIAE | 16.29 |
| SEQ ID NO: 8 | MpAgo | Marinitoga piezophile | YIGIDILSHD-- | LELNEKMNLD | FTLRDGRFI | LHIANKVAL | 14.40 |
| SEQ ID NO: 9 | LrAgo | Limnathrix rosea | IVGLDVSR--- | SIRDAVIDGE | LIHRDGLEP | TYYADKIST | 13.40 |
| SEQ ID NO: 10 | IbAgo | Intestinibacter bartlettii | YIGLDVCR--- | HQSGEKIQIN | VFHRDGINR | TYYADLSSI | 18.04 |
| SEQ ID NO: 11 | CbcAgo | Clostridium butyricum CWBI1009 | FIGLDVGTR-- | PQSGEKIAET | VIHRDGFSR | TGYAD--KI | 15.64 |
| SEQ ID NO: 12 | CpAgo | Clostridium perfringens | FVGLDVGTR-- | PQNGEKINTE | VIHRDGFSR | TGYAD--KI | 16.49 |
| SEQ ID NO: 13 | SeAgo | Synechococcus elongates | IIGFDTGTN-- | VQRGETFSGQ | LLMRDGLVQ | LHLADRSSK | 14.92 |
| SEQ ID NO: 14 | PfAgo | Pyrococcus furiosus | IIGIDVAPM-- | EQRGESVDMN | LLLRDGRIT | VHYAHKFAN | 13.98 |
| SEQ ID NO: 15 | MjAgo | Methanocaldococcus jannaschii | IMGLDTGLG-- | QPIETPAPGE | LPLRDGFIQ | IHYADKFVK | 14.24 |
| SEQ ID NO: 16 | hAgo2 | Homo sapiens | FLGADVTHP-- | VQQHRQEIIQ | IFYRDGVSE | AYYAHLVAF | 14.62 |
| SEQ ID NO: 17 | KpAgo | Kluyveromyces Polysporus | VLGSDVTHY-- | DGPGEEIITN | MYFRDGVSV | VYYADLLCT | 13.85 |
| SEQ ID NO: 18 | MbpAgo | Mucilaginibacter paludis | YIGIDVHDR-- | SQRVEKVRAK | VIVRDGRSF | IKLIDTLLE | 22.58 |
| SEQ ID NO: 19 | VbAgo37 | Verrucomicrobia bacterium | YMGVDLLA--- | RGITEKIDRV | VVHRDGRWW | IRWSDERLR | 100 |
| SEQ ID NO: 20 | VbAgo37_DM | Verrucomicrobia bacterium double mutant | YMGVALLA--- | RGITEKIDRV | VVHRAGRWW | IRWSDERLR | |

FIG. 2

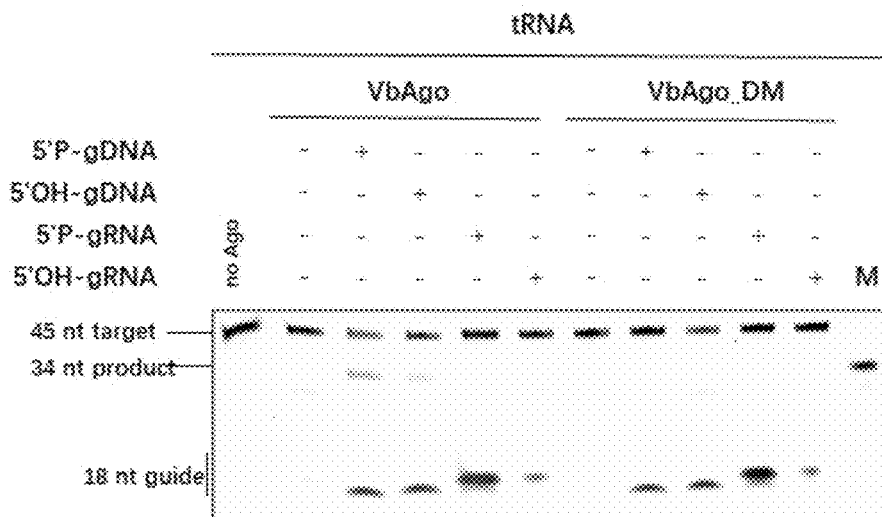
FIG. 4
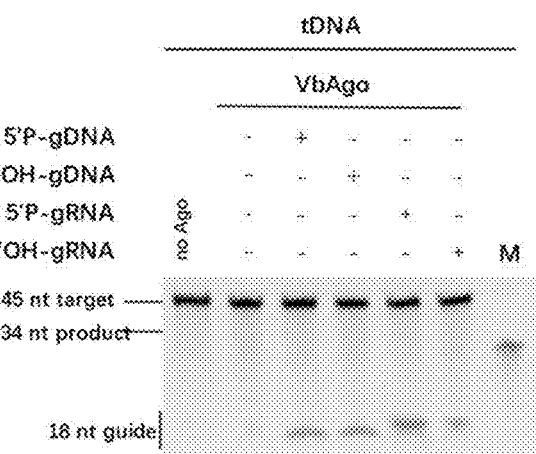
FIG. 5
SEQ ID NO: 21 gDNA 5' T G A G G T A G T A G G T T G T A T
                     | | | | | | | | | | | | | | | | | |
SEQ ID NO: 22 rRNA 3' U A C U C C A U C A U C C A A C A U A U C A U U C G A A C C G U G A C C G G C A G C A A A
FIG. 6
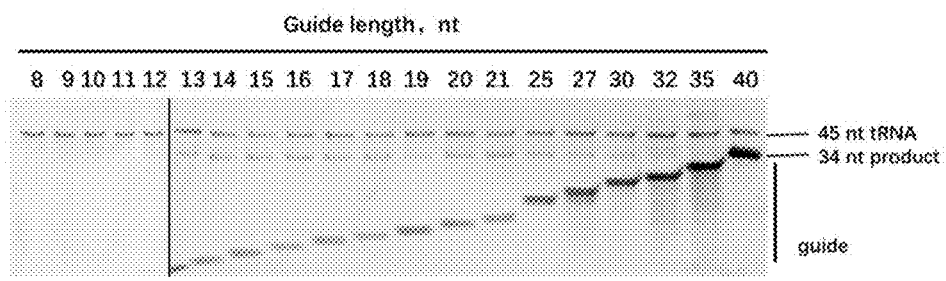
FIG. 7

SEQUENCE LISTING

```
Sequence total quantity: 22
SEQ ID NO: 1            moltype = AA  length = 782
FEATURE                 Location/Qualifiers
source                  1..782
                        mol_type = protein
                        organism = synthetic construct
SEQUENCE: 1
```

```
MSEKQLGATL FPITGLPAQA FRLRVLRVRE TIPMDTQTPV RLNRWATQLW KELKQAVVPT  60
GRFEWPAFLT PDVESLTVGR VLTVQDVPDR EYSIEVIGET VEVNPASASS EELQLAGEMI 120
KRAISDAFGR NSDKYWRKHW NLYFRLEPEN LQDRRDRVFA YRGLKFSVVF LGDKPWLAAD 180
ILTTYHGQHA LSEYSSEQRQ RELHFHVSER IEADDRAMFL RDNGKIKIPC RFVGSTGKTV 240
TQYTFPINGG QKNVREYYEQ RYGIRVPEND EAVFVRDREG CDSWPVPASR LFPLFTTEYD 300
EVRNCSVVPQ MPPDERVETI RAFLNDLRDV SFAGSTLAIG HSHFQTAERS VFPAPALEFG 360
NGQTLTVDAS LPIEEGYNRY RQGKMTMLYE HGPFSSQSLP DLVLLYPDNL DRNAREKLRQ 420
RLGEEIKELC GVAPRIARQI SYPLGKQPHA GAGLLAAADE LVRNNDGTFL PVIVLADALR 480
EHIYDLLKRR LSSLASQCVR ERTVARVARD EQAVGGSRLR NLALGILTAA GLQPWVLAKP 540
LHYDFYMGVD LLANQVIYVF VCGKGGRNVW VQRGDQLRRR GITEKIDRVQ LADQFKTGVR 600
EAKRLGVPLN SLVVHRDGRW WSNEDLAITE AVAELQGDGT LSKDCQVGVV EVRKSHLPVR 660
LFSVLNATKG SLENPMPGSH LILNNTEAIL TPTGQPGRWD KQGRTAGTLL LRITRNPNGS 720
PLDIRKIAED AYGLTHLNWN APDIEISLPV TIRWSDERLR EIVTNPSATD DTEVEPQETC 780
IV                                                              782

SEQ ID NO: 2            moltype = DNA  length = 2346
FEATURE                 Location/Qualifiers
source                  1..2346
                        mol_type = other DNA
                        organism = synthetic construct
SEQUENCE: 2
atgagcgaaa aacagctggg ggcgacctta ttcccgatta ccggcctgcc cgcacaggca   60
tttcggctgc gcgttctgcg ggtgcgggaa accattccga tggacaccca gaccccggtt  120
agactgaacc gctgggcaac ccagctgtgg aaagagctga agcaagcagt tgtcccgacc  180
ggtcgttttg aatggcctgc gttcttaacc cccgatgtgg aaagcttaac agttggtcgg  240
gttctgactg ttcaggatgt acctgatcgg gaatatagca tcgaagttat tggtgaaaca  300
gttgaggtga atcctgcatc tgcatccgtca gaagaactgc agctggcagg gaaaatgatt  360
aaaacgcgca attagcgatgc cttttggtaga aacagcgaca atattggag aaaacattgg  420
aatctgtact tcgtctggaa accggaaaat ctgcaagatc gtcgtgatag agtgtttgca  480
tatcgtggtt taaagtttag cgttgtgttc ctgggtgaca agccgtggct ggcagcggac  540
attcttacca cctatcatgg tcagcatgca ctgtcagaat atagcagcga acagcgtcag  600
agaactgcac ttttcacgt tagtgagcgt attgaagcag atgatcgtgc aatgttttta  660
cgtgacaacg gcaaaataaa atcccatgt cgttttgtgg gatcaaccgg taaaaccgtt  720
acccaataca cctttccgat taatggtggt cagaagcagt gttcgtaata ttacgagcaa  780
cgttatggta tccgtgtgcc ggagaatgat gaagcagtgt ttgttcgtga tagagaaggc  840
tgtgatagct ggccggttcc cgcaagtcgt ctgttcccgc tgtttaccac cgaatatgat  900
gaagtgcgga attgtagcgt tgtgcctcag atgccgccgg atgaacgtgt tgagactatt  960
agagcatttc tgaatgattt acgggatgtt tcttttgcag cagcaccct ggcgattggt 1020
catagccatt ttcagaccgc agaacgtagc gttttttccgg cacctgcatt agaatttggt 1080
aatggtcaaa ccctgaccgt tgatgcatct ttaccgattg aagagggtta taacagatac 1140
cgtcaggta aaatgaccat gttatatgaa catggtccgt ttagtagcca gagcctgccg 1200
gatttagttc tgctgtatcc ggataatctg gatcgcaatg cacgtgagaa actgcgccaa 1260
cgtctgggag aagaaattaa agaactgtgt ggggttgctc cggcgattgc agtcaaatt 1320
agctatcctt taggcaaaca accgcatgca ggtgccggtc tgctggcagc agcagatgaa 1380
ttagttagaa ataatgatgg aaccttcctg ccggttattg ttctggcaga tgcactgcgc 1440
gaacatatct atgatttact taaacgtcgt ctgagctcac ttgcaagcca atgtgttcgt 1500
gagcgaccg tggcacgtgt tgcccgtgat gagcaggcgg ttggtggaa ccgtcttcgt 1560
aacctggccc tgggtatcct gaccgcagca ggactgcagc cgtgggtttt agcaaaaccg 1620
ctgcattatg attttatat gggcgtggat tacttgcga atcaggttat ttatgttttc 1680
gtttgtggta aaggcggtcg taatgtttgg gttcagcgtg gtgatcagct gcgtcgtcgt 1740
ggtattaccg agaagattga tcgtgttcag ttagcagatc agtttaagac cggtgttcgt 1800
gaggcaaaac gtctgggtgt tccgctgaat agcttagttg ttcatcgtga tggtcgttga 1860
tggagcaatg aagattagc tattaccgag gcagttgcag aactgcaggg ggatggtacc 1920
ctgagcaaag attgtcaggt tggtgtggtt gaggttcgta aaagccatct gccggttcgt 1980
ctgttcagtg ttctgaatgc aaccaaagga agtttagaaa atccgatgcc ggggagccat 2040
ctgatcctga ataatacccga agcgattctg accccaccg gtcagcctgg tcgttgggat 2100
aaacagggtc gtaccgcagg tacactgtta cttcgtataa ccagaaaccc gaatggtagc 2160
ccgttagaca tccgcaaaat agcagaagac gcatatggtt taactcatct taattggaat 2220
gcaccggata tcgaaattag cctgcctgtt accattcgct ggagcgatga acgttttacgt 2280
gagattgtga ccaatccgag tgcaaccgat gatacagaag ttgaacctca ggagacctgt 2340
attgtg                                                          2346

SEQ ID NO: 3            moltype = AA  length = 36
FEATURE                 Location/Qualifiers
source                  1..36
                        mol_type = protein
                        organism = synthetic construct
SEQUENCE: 3
FIGIDVSHIL AGEKIDDTTI HRDGFWRIHY ADLSAT                            36

SEQ ID NO: 4            moltype = AA  length = 37
FEATURE                 Location/Qualifiers
source                  1..37
                        mol_type = protein
                        organism = synthetic construct
SEQUENCE: 4
AVGFDAGGRA QAGERIPQEL LLRDGRVPLH LADRLVK                           37

SEQ ID NO: 5            moltype = AA  length = 35
```

```
FEATURE                 Location/Qualifiers
source                  1..35
                        mol_type = protein
                        organism = synthetic construct
SEQUENCE: 5
FIGLDVGTRP QSGEKIAETV IHRDGFSRTG YADKI                          35

SEQ ID NO: 6            moltype = AA  length = 37
FEATURE                 Location/Qualifiers
source                  1..37
                        mol_type = protein
                        organism = synthetic construct
SEQUENCE: 6
FIGIDVSRSP QLGEKLQSTV IHRDGFMNTA YADQAST                        37

SEQ ID NO: 7            moltype = AA  length = 38
FEATURE                 Location/Qualifiers
source                  1..38
                        mol_type = protein
                        organism = synthetic construct
SEQUENCE: 7
VVGMGLAELS EYEGYSDAIR VFHAHRPLKI FYSERIAE                       38

SEQ ID NO: 8            moltype = AA  length = 37
FEATURE                 Location/Qualifiers
source                  1..37
                        mol_type = protein
                        organism = synthetic construct
SEQUENCE: 8
YIGIDLSHDL ELNEKMNLDF ILRDGREILH IANKVAL                        37

SEQ ID NO: 9            moltype = AA  length = 36
FEATURE                 Location/Qualifiers
source                  1..36
                        mol_type = protein
                        organism = synthetic construct
SEQUENCE: 9
IVGLDVSRSI RDAVIDGELI HRDGLEPTYY ADKIST                         36

SEQ ID NO: 10           moltype = AA  length = 36
FEATURE                 Location/Qualifiers
source                  1..36
                        mol_type = protein
                        organism = synthetic construct
SEQUENCE: 10
YIGLDVCRHQ SGEKIQINVF HRDGINRTYY ADLSSI                         36

SEQ ID NO: 11           moltype = AA  length = 35
FEATURE                 Location/Qualifiers
source                  1..35
                        mol_type = protein
                        organism = synthetic construct
SEQUENCE: 11
FIGLDVGTRP QSGEKIAETV IHRDGFSRTG YADKI                          35

SEQ ID NO: 12           moltype = AA  length = 35
FEATURE                 Location/Qualifiers
source                  1..35
                        mol_type = protein
                        organism = synthetic construct
SEQUENCE: 12
FVGLDVGTRP QNGEKINTEV IHRDGFSRTG YADKI                          35

SEQ ID NO: 13           moltype = AA  length = 37
FEATURE                 Location/Qualifiers
source                  1..37
                        mol_type = protein
                        organism = synthetic construct
SEQUENCE: 13
IIGFDTGTNV QRGETFSGQL LMRDGLVQLH LADRSSK                        37

SEQ ID NO: 14           moltype = AA  length = 37
FEATURE                 Location/Qualifiers
source                  1..37
                        mol_type = protein
                        organism = synthetic construct
SEQUENCE: 14
IIGIDVAPME QRGESVDMNL LLRDGRITVH YAHKFAN                        37
```

```
SEQ ID NO: 15           moltype = AA  length = 37
FEATURE                 Location/Qualifiers
source                  1..37
                        mol_type = protein
                        organism = synthetic construct
SEQUENCE: 15
IMGLDTGLGQ PIETPAPGEL FLRDGFIQIH YADKFVK                              37

SEQ ID NO: 16           moltype = AA  length = 37
FEATURE                 Location/Qualifiers
source                  1..37
                        mol_type = protein
                        organism = synthetic construct
SEQUENCE: 16
FLGADVTHPV QQHRQEIIQI FYRDGVSEAY YAHLVAF                              37

SEQ ID NO: 17           moltype = AA  length = 37
FEATURE                 Location/Qualifiers
source                  1..37
                        mol_type = protein
                        organism = synthetic construct
SEQUENCE: 17
VLGSDVTHYD GPGEEIITNM YFRDGVSVVY YADLLCT                              37

SEQ ID NO: 18           moltype = AA  length = 37
FEATURE                 Location/Qualifiers
source                  1..37
                        mol_type = protein
                        organism = synthetic construct
SEQUENCE: 18
YIGIDVHDRS QRVEKVRAKV IVRDGRSFIK LIDTLLE                              37

SEQ ID NO: 19           moltype = AA  length = 36
FEATURE                 Location/Qualifiers
source                  1..36
                        mol_type = protein
                        organism = synthetic construct
SEQUENCE: 19
YMGVDLLARG ITEKIDRVVV HRDGRWWIRW SDERLR                               36

SEQ ID NO: 20           moltype = AA  length = 36
FEATURE                 Location/Qualifiers
source                  1..36
                        mol_type = protein
                        organism = synthetic construct
SEQUENCE: 20
YMGVALLARG ITEKIDRVVV HRAGRWWIRW SDERLR                               36

SEQ ID NO: 21           moltype = DNA  length = 18
FEATURE                 Location/Qualifiers
source                  1..18
                        mol_type = other DNA
                        organism = synthetic construct
SEQUENCE: 21
tgaggtagta ggttgtat                                                  18

SEQ ID NO: 22           moltype = RNA  length = 45
FEATURE                 Location/Qualifiers
source                  1..45
                        mol_type = other RNA
                        organism = synthetic construct
SEQUENCE: 22
tactccatca tccaacatat cattcgaacc gtgaccggca gcaaa                    45
```

APPLICATION OF PROKARYOTIC ARGONAUTE PROTEIN WITH ONLY RNA TARGET CLEAVAGE ACTIVITY IN RNA EDITING

TECHNICAL FIELD

The disclosure relates to the technical field of molecular biology, and more particularly to an application of a prokaryotic Argonaute protein (pAgo) derived from prokaryotes with only ribonucleic acid (RNA) target cleavage activity in RNA editing in vivo or in vitro.

STATEMENT REGARDING SEQUENCE LISTING

The sequence listing associated with this application is provided in text format in lieu of a paper copy and is hereby incorporated by reference into the specification. The name of the XML file containing the sequence listing is 23006JHG-USP1-SL.xml. The XML file is 23,586 bytes; is created on Nov. 2, 2023; and is being submitted electronically via EFS-Web.

BACKGROUND

At present, eukaryotic Argonaute proteins (eAgos) are able to catalyze RNA cleavage reactions guided by guide ribonucleic acids (gRNAs) under ambient conditions and play a crucial role in the RNA interference (RNAi) pathway. Compared with the eAgos, prokaryotic Argonaute proteins (pAgos) have more diverse functions and structures, but their physiological functions have been elusive for a long time. Early studies mainly focused on the pAgos derived from thermophilic organisms, except for MpAgo derived from *Marinitoga piezophila*, which prefers to cleave single-stranded DNA (ssDNA) targets and RNA targets with 5'-hydroxylated (5'-OH) gRNA, the rest of pAgos from thermophilic organisms prefer to cleave ssDNA targets and/or RNA targets with 5'-phosphorylated (5'-P) gDNA. However, the pAgos derived from thermophilic organisms have only low levels of gDNA-guided ssDNA target and/or RNA target cleavage activity under mesophilic conditions, which limits the application and development of pAgos-based gene editing and RNA editing technologies. Recent studies have focused on pAgos derived from mesophilic organisms in order to find pAgos that can effectively cleave the DNA targets and/or the RNA targets under mesophilic conditions. However, almost all characterized mesophilic pAgos prefer to cleave the DNA targets under the guidance of gDNA at moderate temperatures, and there are few reports of pAgos that can effectively cleave the RNA targets. NgAgo derived from halobacterium *Natronobacterium gregory* can cleave the RNA targets under the guidance of gDNA at room temperature, but its cleavage site is still uncertain, and it has not been proven to cleave highly-structured RNA. KmAgo derived from the mesophilic bacterium *Kurthiamas siliensis* can cleave the DNA targets and the RNA targets under the guidance of gDNA and gRNA, but it prefers to cleave the DNA targets. MbpAgo derived from the psychrotrophic bacterium *Mucilaginibacter paludis* prefers to cleave the RNA targets under the guidance of gDNA, but still retains the activity of cleaving the DNA targets. So far, pAgos that can specifically cleave RNA targets has not been reported.

For a long time, people have paid extensive attention to programmable endonucleases targeting RNA, because these enzymes can be applied to the research of RNA structure and function, nucleic acid detection, RNA nanotechnology, RNA therapy and other fields. The methods currently used have certain limitations. A clustered regularly interspaced short palindromic repeats-CRISPR-associated proteins (CRISPR-Cas) system is currently the most widely used enzyme tool for programmable nucleic acid cleavage. The newly discovered CRISPR-Cas13 nucleases are rapidly being applied to many fields, including RNA editing, virus clearance, and nucleic acid detection. However, CRISPR-Cas nucleases require gRNA guides, and RNA is mainly prepared by in vitro transcription and purification, or by chemical synthesis, which is costly. In addition, these nucleases have not yet been shown the ability to recognize structured RNA elements. Some eAgos can also cleave almost all types of RNA at moderate temperature under the guidance of gDNA, but there are RNAi pathways in most animal and plant cells, these eAgos may interfere with the RNAi function of the cell itself, which hinders the application of eAgos to intracellular RNA editing. However, there is no RNAi pathway in prokaryotic organisms, the pAgos may not affect the RNAi function of cells themselves. Therefore, there is still an urgent need in the field of RNA editing for pAgos that can function under room temperature and can be applied to RNA editing of the animal and plant cells.

RNA editing refers to the process of changing genetic information at the messenger RNA (mRNA) level. RNA editing is associated with biological cell development and differentiation, and is an important way of regulating gene expression. However, based on the above statements, it is known that the existing RNA editing technology still has the following problems and defects. 1. Although the existing pAgos proteins can effectively target and cleave various kinds of RNAs at room temperatures and can be applied to RNA editing of the animal and plant cells, they also exhibit DNA cleavage activity, which may cause damage to intracellular DNA. 2. General RNAi technology requires the use of double-stranded RNA (dsRNA), chemical synthesis of dsRNA is expensive and has a long customization cycle, and in vitro transcription of dsRNA is relatively inexpensive but has cumbersome and time-consuming procedures. 3. The gene interference effect of short hairpin RNA (shRNA) expression plasmid is long-lasting and economical, but the preparation is time-consuming and there is non-specific gene repression. 4. CRISPR-based technology also needs to use long gRNAs, which has the same problems as the RNAi technology. In addition, CRISPR-associated proteins (e.g., Cas13a) rely on special motifs near a target site to recognize and bind the target, which limits the scope of editing, and CRISPR-associated proteins also have very strong non-specific "collateral cleavage" activity, which raises concerns about possible off-target reactions.

SUMMARY

In view of the above problems in the related art, the disclosure provides a technique for cleaving an RNA target, which is simple in operation, low-cost, efficient and specific.

In order to achieve the above purpose, technical solutions of the disclosure are as follows.

An Argonaute protein derived from a mesophilic prokaryote *Verrucomicrobia bacterium*, named VbAgo, has binding activity to a single-stranded guide DNA (gDNA) and nuclease activity only to an RNA target complementary to single-stranded gDNA, so it can perform specific cleavage to the RNA target. The amino acid sequence of the above VbAgo is shown in SEQ ID NO: 1, and the gene sequence encoding VbAgo is shown in SEQ ID NO: 2.

The substitution and/or deletion of one or more amino acids in sites 181-306, and/or 386-548, and/or 549-782 of the amino acid sequence of VbAgo is still expected to obtain a VbAgo mutant protein with the same function as VbAgo.

Figure 12:
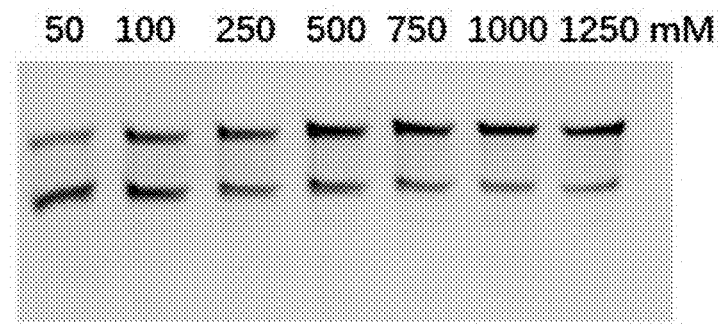

The above sites are key sites for the catalytic activity of VbAgo. By one or more amino acid residues essential to the catalytic activity of VbAgo can form a new nuclease activity that has the potential to increase or decrease its endonuclease activity, but also has the potential to result in the absence of endonuclease activity. The mutant lacking endonuclease activity still has binding activity to single-stranded DNA (ssDNA) guide, which can broaden its application.

In the above technical solution, the RNA target that can be specifically cleaved by the VbAgo and the VbAgo mutant protein may be an RNA target with an advanced structure (also referred to as highly-structured RNA target) or an RNA target without the advanced structure. Specifically, the RNA target may be in vitro transcribed RNA, viral genomic RNA, messenger RNA (mRNA), or other kinds of intracellular RNA.

The disclosure further provides a method for RNA editing in vivo and in vitro using the VbAgo or the VbAgo mutant protein that specifically cleaves an RNA target, specifically including that: an Argonaute protein, a gDNA and an RNA target are added into a reaction system for specific cleavage reaction.

In an embodiment, the gDNA is one of 5'-phosphorylated ssDNA and 5'-hydroxylated ssDNA. In a specific embodiment, when the 5'-end of the gDNA is phosphorylated, the nuclease activity of the complex on the RNA target is higher.

In an embodiment, a length of gDNA is in a range of 13 to 35 nucleotides. In a specific embodiment, the length of gDNA is in a range of 15 to 20 nucleotides.

In an embodiment, the reaction system includes at least one cation of $Mn^{2+}$, $Mg^{2+}$, $Ni^{2+}$. In an embodiment, the cation is selected as at least one of $Mn^{2+}$ and/or $Mg^{2+}$. For example, when the 5'-end of the gDNA is phosphorylated, a concentration of $Mn^{2+}$ is at least 0.1 millimoles per liter (mM) and a concentration of $Mg^{2+}$ is at least 1 mM.

In an embodiment, in an application process of the RNA editing, a reaction temperature is in a range of 25-65° C. In a specific embodiment, the reaction temperature is in a range of 37-60° C.

In an embodiment, the reaction system for the RNA editing includes sodium chloride at a concentration in a range of 50-1250 mM. In a specific embodiment, the Argonaute protein provided by the disclosure has higher cleavage efficiency when the concentration of the sodium chloride is 50 mM, and can achieve 90% cleavage efficiency.

The VbAgo or the VbAgo mutant protein and it complex with gDNA can be used to prepare an RNA editing kit. It is understandable that in this kit, the VbAgo or the VbAgo mutant protein and its corresponding gDNA may be packaged after complexing or separately packaged.

Compared with the related art, the disclosure has the following beneficial effects.

1) The disclosure provides the Argonaute protein that can effectively and exclusively cleave RNA, which can be used for in vivo and in vitro targeted RNA editing to further perform specific site modification on genetic materials. It is a novel and effective tool, and greatly promotes the development of the field of RNA editing.
2) The Argonaute protein provided by the disclosure does not rely on a special motif near the target site to recognize and bind the target sequence, so the gDNA design is easy to design without considering site constraints; and compared with conventional gRNAs, the synthesis of the gDNA has a short cycle time and is low-cost, resulting in great cost savings.
3) The Argonaute protein provided by the disclosure has strong cleavage activity and is strictly dependent on the complementary pairing of the guide and the target to exert cleavage activity. There is no nonspecific "collateral cleavage" activity such as CRISPR related protein, and the specificity is better.
4) The nuclease active site of the Argonaute protein provided by the disclosure can be mutated to obtain a prokaryotic Argonaute protein (pAgo) that completely loses cleavage activity, which can fuse other effector proteins and further expand its application.
5) The Argonaute protein provided by the disclosure is only about three-quarters of the size of eukaryotic Argonaute proteins (eAgos) and one-half of clustered regularly interspaced short palindromic repeats (CRISPR)-associated proteins, which is easier to transfect into cells.

BRIEF DESCRIPTION OF DRAWINGS

FIG. 1 illustrates a schematic diagram of an evolutionary tree of *Verrucomicrobia bacterium* derived Argonaute protein (VbAgo) and some characterized Argonaute proteins according to the disclosure.

FIG. 2 illustrates a schematic diagram of a catalytic DEDX tetrad sequence comparison of the VbAgo, VbAgo_DM and the some characterized Argonaute proteins according to an embodiment 1 of the disclosure.

FIG. 3 illustrates a detection diagram of the VbAgo and the VbAgo_DM by sodium dodecyl-sulfate polyacrylamide gel electrophoresis (SDS-PAGE) according to the embodiment 1 of the disclosure.

FIG. 4 illustrates a diagram showing results of detecting cleavage activities of the VbAgo and the VbAgo_DM binding to different guides on an RNA target according to an embodiment 2 of the disclosure.

FIG. 5 illustrates a diagram showing results of detecting the cleavage activity of the VbAgo binding to the different guides on a DNA target according to the embodiment 2 of the disclosure.

FIG. 6 illustrates a schematic sequence diagram of the RNA target and a single-stranded DNA (ssDNA) guide used for testing according to the embodiment 2 of the disclosure.

FIG. 7 illustrates a diagram showing results of detecting products of cleavage of the RNA target by binding of gDNAs of different lengths to the VbAgo by urea polyacrylamide gel electrophoresis (urea-PAGE) according to an embodiment 3 of the disclosure.

FIG. 8 illustrates a diagram showing results of detecting effects of different divalent metal cations on the activity of the VbAgo cleaving the RNA target by the urea-PAGE according to an embodiment 4 of the disclosure.

FIG. 9 illustrates a diagram showing results of detecting effects of manganese cation ($Mn^{2+}$) concentrations on the activity of the VbAgo cleaving the RNA target by the urea-PAGE according to the embodiment 4 of the disclosure.

FIG. 10 illustrates a diagram showing results of detecting effects of magnesium cation ($Mg^{2+}$) concentrations on the activity of the VbAgo cleaving the RNA target by the urea-PAGE according to the embodiment 4 of the disclosure.

FIG. 11 illustrates a diagram showing results of detecting effects of reaction temperature on the activity of the VbAgo cleaving the RNA target by the urea-PAGE according to an embodiment 5 of the disclosure.

FIG. 12 illustrates a diagram showing results of detecting effects of sodium chloride concentrations on the activity of the VbAgo cleaving the RNA target by the urea-PAGE according to an embodiment 6 of the disclosure.

Figure 13:
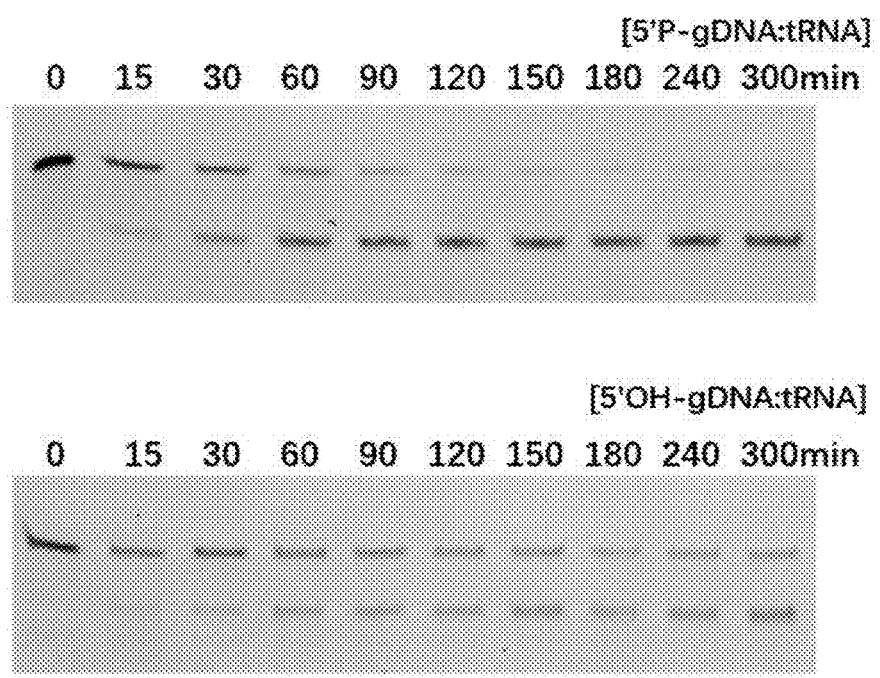

FIG. 13 illustrates a diagram showing results of detecting effects of reaction time on the activity of the VbAgo cleaving the RNA target by the urea-PAGE according to an embodiment 7 of the disclosure.

DETAILED DESCRIPTION OF EMBODIMENTS

Technical solutions of the disclosure will be clearly and completely described below in connection with embodiments in the disclosure. Apparently, the described embodiments are only some embodiments of the disclosure and not all of them. Based on the embodiments of the disclosure, all other embodiments obtained by the those skilled in the related art without making creative labor are within the scope of protection of the disclosure.

Embodiment 1

In this embodiment, VbAgo is obtained by recombinant expression and purification based on a sequence encoding an Argonaute protein obtained from a mesophilic prokaryote *Verrucomicrobia bacterium*. The process is as follows.

The nucleotide sequence as shown in SEQ ID NO: 2 is synthesized and ligated to pET23a by a conventional cloning method to obtain a pET23a-VbAgo plasmid, and then the pET23a-VbAgo plasmid is transformed into *Escherichia coli* BL21 (DE3). A single colony is inoculated into a Luria-Bertani (LB) liquid medium containing 100 micrograms per milliliters (μg/mL) of ampicillin, cultured in a shaker at 37° C. and 220 revolutions per minute (rpm), and when the optical density at 600 nanometers ($OD_{600}$) reaches 0.8, the bacteria are transferred to 18° C. shaker and induced by isopropylthio-β-galactoside (IPTG) overnight. The bacteria are collected by centrifugation at 6000 rpm for 10 minutes (min). After washing with a buffer A (20 millimoles per liter, abbreviated as mM, Tris-HCl, pH 7.5, 500 mM sodium chloride, abbreviated as NaCl), the bacteria are suspended in the buffer A, with the addition of phenylmethanesulfonyl fluoride (PMSF) at a final concentration of 1 mM, and crushed under high pressure. The crushed mixture is centrifuged at 18000 rpm for 30 min and then the supernatant is collected.

After the supernatant is filtered, nickel-nitrilotriacetic acid (Ni-NTA) purification is performed. 10 column volumes are washed with the buffers A containing 10 mM imidazole and 20 mM imidazole respectively (added in three times), and then 3 column volumes are washed with buffers containing 50 mM, 80 mM, 100 mM, 150 mM, 200 mM, 250 mM, 300 mM, and 1 mole per liter (M) imidazole respectively. The eluate is detected by sodium dodecyl-sulfate polyacrylamide gel electrophoresis (SDS-PAGE), elution fractions containing high purity target proteins are collected, and ultrafiltered to a buffer B (20 mM HEPES-NaOH, pH 7.5, 500 mM NaCl). A heparin column (HiTrapHeparinHP, GE Healthcare) purification is performed after diluting the NaCl concentration of the protein is diluted to 125 mM with 20 mM HEPES-NaOH pH 7.5. The heparin column is pre-equilibrated with a buffer C (20 mM HEPES-NaOH, pH 7.5, 125 mM NaCl), and the VbAgo is eluted by increasing the concentration of NaCl. The purified protein is collected, the purity is identified and analyzed by SDS-PAGE, and the protein is divided into small portions, which are quickly frozen in liquid nitrogen and stored at −80° C. The evolutionary tree of the VbAgo and some characterized Argonaute proteins (referred to as Ago proteins) is shown in FIG. 1. A catalytic DEDX tetrad of VbAgo is the $546^{th}$-$553^{rd}$, $580^{th}$-$589^{th}$, $613^{th}$-$621^{st}$ and $752^{nd}$-$760^{th}$ sites of the sequence shown in SEQ ID NO: 1, respectively. In this embodiment, the first and third D (i.e., aspartic acid) in the catalytic DEDX tetrad of VbAgo are further mutated to A (i.e., alanine), and the double mutant is obtained by the above VbAgo expression and purification method, which is recorded as VbAgo_DM. The schematic diagram of the catalytic DEDX tetrad sequence comparison (see SEQ ID NOs: 3-20) of the VbAgo, the VbAgo_DM, and sixteen characterized Agos is shown in FIG. 2.

Figure 3:
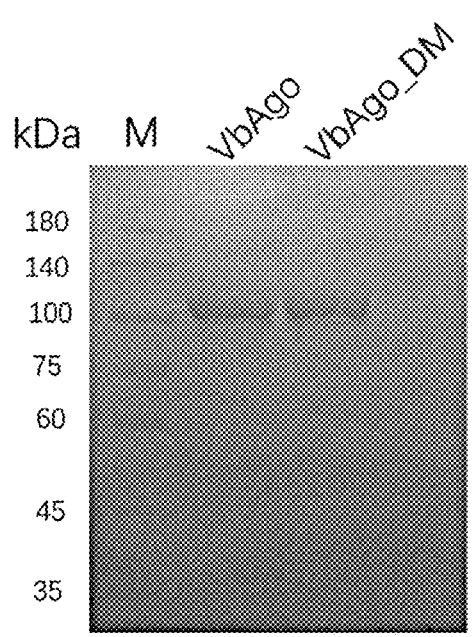

According to the calculation through a website of expasy, the expected size of VbAgo is 88.3 kilodalton (kDa), and its amino acid sequence is shown in SEQ ID NO: 1. The SDS-PAGE identification analysis results (FIG. 3) are consistent with the calculation results.

Embodiment 2

To evaluate the specificity of the VbAgo and the VbAgo_DM to a guide nucleic acid and an RNA target, and the activity of all possible combinations is determined in this embodiment. The cleavage test of this embodiment is carried out at 37° C. with a molar ratio of 4:2:1 (pAgo:guide:target), specifically as follows.

800 nanomoles per liter (nM) VbAgo and 400 nM guide are first mixed with reaction buffer containing 10 mM HEPES-NaOH (pH 7.5), 100 mM NaCl, 5 mM manganese chloride ($MnCl_2$) and 5% glycerol, and incubated at 37°C for 10 min for guide loading. The RNA target or the DNA target is added at a final concentration of 200 nM, and after 1 hour of reaction at 37°C, the reaction is stopped by mixing the reaction solution with 2×RNA loading dye (95% formamide, 18 mM ethylenediaminetetraacetic acid (EDTA), 0.025% Sodium Dodecyl Sulfate (SDS) and 0.025% bromophenol blue) and heating at 95° C. for 5 min. The lysates are analyzed by 20% urea polyacrylamide gel, stained with SYBR™ Gold (Invitrogen), and imaged by a Gel Doc™ XR+ (Bio-Rad) imaging system.

The detection results are shown in FIG. 4 and FIG. 5. 1. The 34-nucleotide (nt) product band is not observed in the DNA/RNA (guide/target) control incubated in the absence of VbAgo, suggesting that the product band is generated by the target molecule cleaved by the VbAgo. 2. VbAgo can cleave the RNA target using 5'-phosphorylated (5'-P) gDNA and 5'-hydroxylated (5'-OH) gDNA. 3. VbAgo_DM loses the activity of cleaving the RNA target, indicating that mutation of at least one amino acid located in an evolutionarily conserved amino acid tetrad can change the catalytic activity of the VbAgo (such as loss of endonuclease activity), that is, the catalytic DEDX tetrad is the key site of VbAgo catalytic activity. 4. VbAgo cannot cleave the DNA target using gDNA or gRNA.

FIG. 6 is a schematic diagram of the gDNA (as shown in SEQ ID NO: 21) cleaving the RNA target (i.e., tRNA as shown in SEQ ID NO: 22) in this embodiment, and the arrow in the FIG. 6 indicates a predicted cleavage site.

Embodiment 3

The effects of divalent metal cations in a reaction system on the cleavage effect are detected according to the cleavage test procedure in the embodiment 2. Specifically, the VbAgo is mixed with 5'-phosphorylated gDNA in a reaction buffer containing 10 mM HEPES-NaOH, pH 7.5, 100 mM NaCl, 5 mM divalent metal cations and 5% glycerol, and incubated at 37° C. for 10 min for guide loading. Then, the target molecule is added for cleavage activity detection. The divalent metal cations are selected from the group consisting of Mn2+, Mg2+, Ca2+, Cu2+, Fe2+, Co2+, Zn2+ and Ni2+.

The product detection method is the same as that of the embodiment 2. The detection results are shown in FIG. 7. The length of gDNA has a certain impact on the activity of VbAgo to recognize and cleave the RNA target, and when the length of gDNA is 15-35 nt, it can effectively cleave the RNA target.

Embodiment 4

The effects of divalent metal cations in a reaction system on the cleavage effect are detected according to the cleavage test procedure in the embodiment 2. Specifically, the VbAgo is mixed with 5'-phosphorylated gDNA in a reaction buffer containing 10 mM HEPES-NaON, pH 7.5, 100 mM NaCl, 5 mM divalent metal cations and 5% glycerol, and incubated at 37° C. for 10 min for guide loading. Then, the target molecule is added for cleavage activity detection. The divalent metal cations are selected from the group consisting of $Mn^{2+}$, $Mg^{2+}$, $Ca^{2+}$, $Cu^{2+}$, $Fe^{2+}$, $Co^{2+}$, $Zn^{2+}$ and $Ni^{2+}$.

Figure 8:
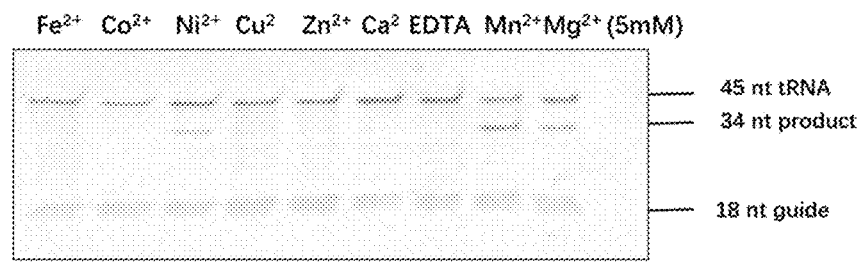

The product detection method is the same as that of the embodiment 2. The detection results are shown in FIG. 8. The choice of the divalent metal cations has a certain impact on the cleavage activity of VbAgo, in which the RNA target can be cleaved under the conditions of $Ni^{2+}$, $Mn^{2+}$, and $Mg^{2+}$.

Figure 9:
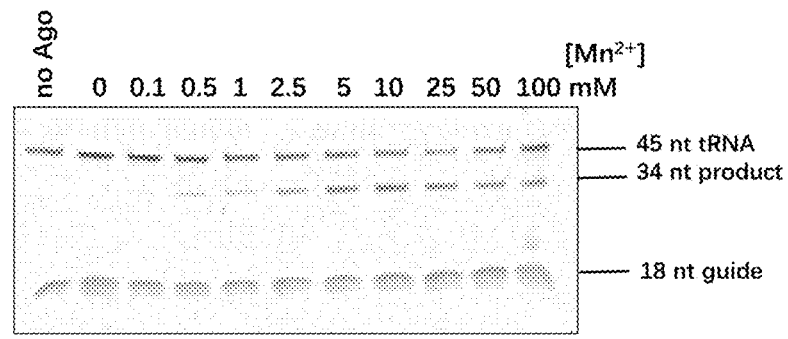
Figure 10:
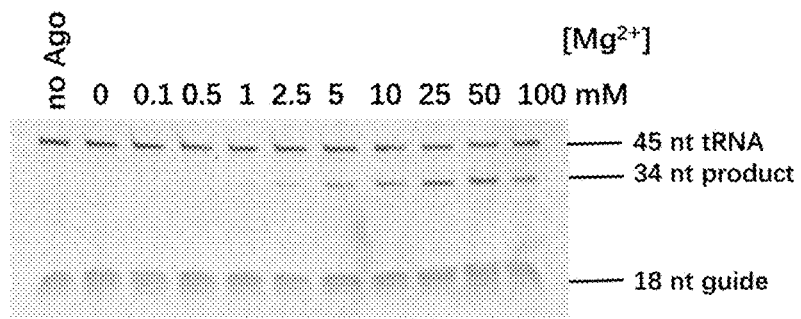

This embodiment further explores the minimum concentration of the divalent metal cations, specifically as follows. The reaction buffers containing $Mn^{2+}$ or $Mg^{2+}$ with concentrations ranging from 0.1 mM to 100 mM are selected, and the others are the same as those in the embodiment 2. The detection results are shown in FIG. 9 and FIG. 10. The concentration of the divalent metal cations has a certain impact on the cleavage activity of the VbAgo. When the guide is 5'-phosphorylated DNA, the minimum concentration of $Mn^{2+}$ is 0.1 mM or the minimum concentration of $Mg^{2+}$ is 1 mM, it can efficiently cleave the RNA target, that is, the addition concentration of $Mn^{2+}$ should be greater than or equal to 0.1 mM, while the addition concentration of Mg' should be greater than or equal to 1 mM.

Embodiment 5

The effect of the temperature of the reaction system on the cleavage effect is detected according to the cleavage test procedure in the embodiment 2. Specifically, the VbAgo is first incubated with 5'-phosphorylated gDNA to form a complex, then the target molecule is added, and then the reaction is carried out at a temperature in a range of 25-80° C. for 1 hour.

Figure 11:
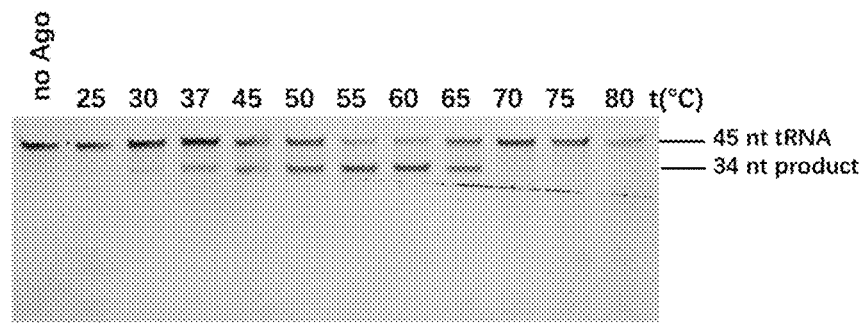

The product detection method is the same as that of the embodiment 2. The detection results are shown in FIG. 11.

When the reaction temperature is in a range of 25-65° C., the VbAgo can cleave the RNA target, and the cleavage activity is relatively high at 37-60° C. Therefore, the VbAgo provided by the disclosure can cleave target genes under a wide range of temperature conditions.

Embodiment 6

The effect of NaCl concentrations in the reaction buffer on the cleavage effect is detected according to the cleavage test procedure in the embodiment 2. Specifically, the VbAgo, the 5'-phosphorylated guide DNA are mixed with a reaction buffer containing 10 mM HEPES-NaOH, pH 7.5, 5 mM $Mn^{2+}$, and 5% glycerol, in which the reaction buffer also contained NaCl with concentrations ranging from 50 mM to 1250 mM, incubated at 37° C. for 10 min for guide loading, and then the target molecule is added to react at 37° C. for 1 hour.

The product detection method is the same as that of the embodiment 2. The detection results are shown in FIG. 12. The NaCl concentration has a certain impact on the cleavage activity of the VbAgo. The cleavage activity of VbAgo decreases when the NaCl concentration is increased. However, when the NaCl concentration is increased to 1 M (i.e., 1000 mM shown in FIG. 12), the cleavage activity of the VbAgo no longer decreases. When the NaCl concentration is 50 mM, the cleavage efficiency can reach about 90%.

Embodiment 7

The effect of reaction time on the cleavage effect is detected according to the cleavage test procedure in the embodiment 2. Specifically, the VbAgo is incubated with 5'-phosphorylated gDNA or 5'-hydroxylated gDNA in the reaction buffer to form a complex, and then the target molecule is added, and then the reaction is carried out at 37° C. for 15-300 min.

The product detection method is the same as that of the embodiment 2, and the detection results are shown in FIG. 13. The VbAgo has better cleavage activity under the guidance of 5'-phosphorylated gDNA, and can cleave the RNA target in about 180 min, while it can only cleave 50% of the RNA target under the guidance of 5'-hydroxylated gDNA.

In summary, the Argonaute protein provided by the disclosure has binding activity to ssDNA guide and nuclease activity to the RNA target, and is capable of editing RNA in vivo and in vitro at low temperature, which is not only simple to operate, low-cost and highly specific, but also has a greater potential for application.

The above mentioned is only specific embodiments of the disclosure, but the protection scope of the disclosure is not limited thereto. Any changes or substitutions that can be readily contemplated by any person skilled in the art within the scope of the art disclosed herein shall be covered within the scope of protection of the disclosure.

What is claimed is:

1. A method of applying a prokaryotic Argonaute protein, comprising:

performing in vitro ribonucleic acid (RNA) editing with the prokaryotic Argonaute protein, wherein the prokaryotic Argonaute protein only has a cleavage activity of a target RNA, and the amino acid sequence of the prokaryotic Argonaute protein is SEQ ID NO: 1;

wherein the prokaryotic Argonaute protein performs a cleavage reaction on the target RNA under a guidance of guide deoxyribonucleic acid (gDNA), and the gDNA is a single-stranded DNA (ssDNA) phosphorylated at a 5'-end; and the reaction system of the cleavage reaction comprises at least one of a manganese cation ($Mn^{2+}$), a magnesium cation ($Mg^{2+}$), and a nickel cation ($Ni^{2+}$); and wherein a length of the gDNA is in a range of 13 to 35 nucleotides.

2. The method according to claim 1, wherein a reaction temperature of the cleavage reaction is in a range of 25 Celsius degrees (C.) to 65° C.

3. The method according to claim 1, wherein the reaction system comprises sodium chloride (NaCl) with a concentration in a range of 50-1250 millimoles per liter (mM).

* * * * *